(12) United States Patent
Weigel et al.

(10) Patent No.: US 8,016,751 B2
(45) Date of Patent: Sep. 13, 2011

(54) OPTICAL INSTRUMENT

(75) Inventors: Martin Weigel, Maulbronn (DE); Alexander Frank, Oberderdingen (DE)

(73) Assignee: Richard Wolf GmbH, Knittlingen (DE)

( * ) Notice: Subject to any disclaimer, the term of this patent is extended or adjusted under 35 U.S.C. 154(b) by 1302 days.

(21) Appl. No.: 11/560,433

(22) Filed: Nov. 16, 2006

(65) Prior Publication Data
US 2007/0112254 A1 May 17, 2007

(30) Foreign Application Priority Data

Nov. 16, 2005 (EP) ..................................... 05025021

(51) Int. Cl.
*A61B 1/00* (2006.01)
(52) U.S. Cl. ......................... 600/130; 600/137; 600/173
(58) Field of Classification Search .................. 600/101, 600/109, 112, 121, 122, 129, 130, 137, 167, 600/173
See application file for complete search history.

(56) References Cited

U.S. PATENT DOCUMENTS

| | | | |
|---|---|---|---|
| 5,569,161 A * | 10/1996 | Ebling et al. .................. | 600/121 |
| 5,575,757 A * | 11/1996 | Kennedy et al. ............... | 600/167 |
| 5,621,830 A | 4/1997 | Lucey et al. | |
| 5,797,836 A * | 8/1998 | Lucey et al. .................. | 600/109 |
| 5,817,014 A | 10/1998 | Hori et al. | |
| 2005/0275725 A1* | 12/2005 | Olsson et al. ............ | 348/207.99 |
| 2006/0167343 A1* | 7/2006 | Peszynski ..................... | 600/146 |

FOREIGN PATENT DOCUMENTS

| | | |
|---|---|---|
| DE | 195 21 654 C2 | 1/1999 |
| EP | 0 592 194 A1 | 4/1994 |

* cited by examiner

*Primary Examiner* — John P Leubecker
*Assistant Examiner* — Samuel Candler
(74) *Attorney, Agent, or Firm* — Panitch Schwarze Belisario & Nadel LLP

(57) ABSTRACT

An optical instrument has an outer shank (15) with a viewing window (31) arranged near the free shank end and a handle part (1) at the other end of the outer shank. An opto-electrical a transducer (26) is rotatably arranged within the outer shank, and is attached on an inner shank (12) which is rotatably mounted within the outer shank. Actuation means (10) for rotating the transducer (26) are provided in the outer shank. An axial bearing is provided between the outer shank and the inner shank (12). Moreover, a spring element impinging the inner shank (12) with force in the direction of the axial bearing is provided.

20 Claims, 3 Drawing Sheets

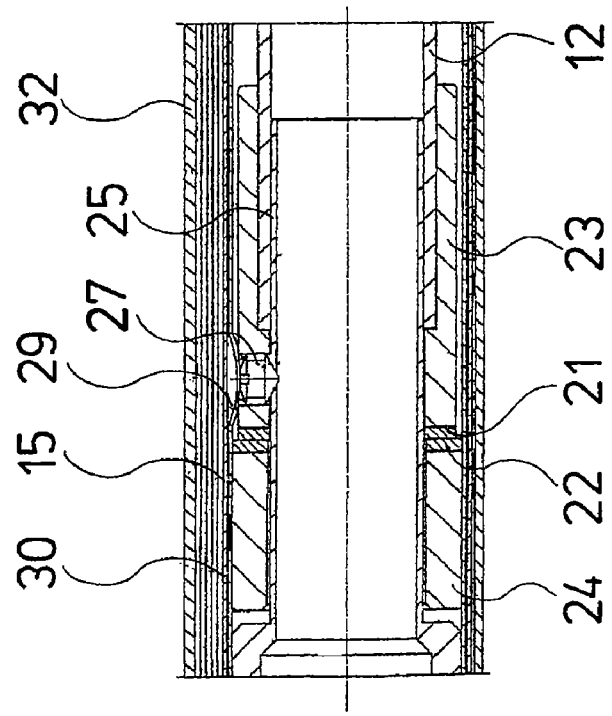
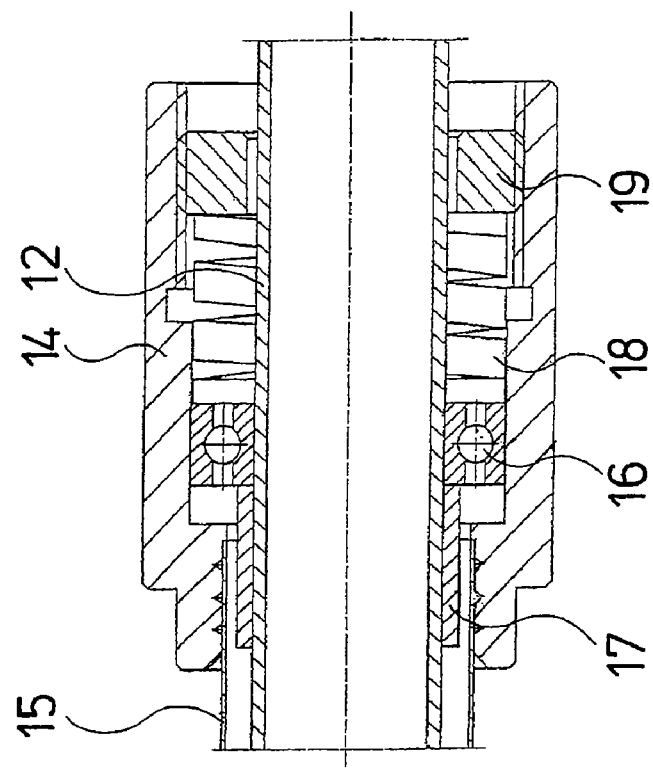

OPTICAL INSTRUMENT

BACKGROUND OF THE INVENTION

The invention relates to an optical instrument, in particular to an endoscope or technoscope, having a shank, a viewing window arranged close to the free shank end, a handle part on the other end of the shank, and an opto-electrical transducer. The transducer is rotatably arranged within the shank.

With such instruments, which are typically provided with lateral viewing optics, i.e., having an optics viewing window arranged at an angle, for example of 30°, to the longitudinal axis, it is within the state of the art to arrange the opto-electrical transducer, typically a CCD-element arranged in a shank, in a rotatable manner. Specifically, the operating person may change the rotational angle of the CCD-transducer to the instrument, typically from the handle part with a wheel or the like located there. This rotational capability is particularly provided to enable alignment of the picture displayed on the monitor in an upright manner again, after the rotation of the instrument about its longitudinal axis. Such an instrument is known for example from U.S. Pat. No. 5,797,836.

Such optical instruments are subjected to high temperatures in a sterilizing device, when applied in the medical field as an endoscope, or in the case of technoscopes, high temperatures may also occur on operation. On the one hand, it is necessary to completely encapsulate the whole instrument with the optics located therein and also any moving parts, but on the other hand, however, it is necessary to provide a sufficient play with regard to the moving parts, so that length changes of the components occurring on account of the temperature fluctuations may be accommodated. An axial play between the CCD-element and the end viewing window may, however, lead to the imaging definition being influenced in an unfavorable manner. With such endoscopic instruments, it is therefore within the state of the art to provide means for the axial adjustment of the CCD-element with respect to the optics. However, one should also take note that with this, whenever possible, the instrument should be hermetically sealed, and with regard to design is quite complicated, and also prone to breakdown.

BRIEF SUMMARY OF THE INVENTION

Against this background, it is an object of the invention to provide an optical instrument of the type mentioned at the outset, such that on the one hand, a rotational capability of the opto-electric transducer with respect to the instrument is possible, but on the other hand, the correct position of the opto-electrical transducer with regard to the optics is always ensured in the direction of the longitudinal axis of the instrument, without an adjustment of the instrument being required. In a further embodiment of the invention, one also ensures that the instrument is sealed with respect to a fiber-optics bundle, which is led through it.

According to the invention, this object is achieved by an optical instrument of the type described at the outset, wherein the opto-electric transducer is attached on an inner shank mounted in a rotatable manner within the outer shank with actuation means for rotating the transducer in the outer shank, and wherein an axial bearing and at least one spring element impinging the inner shank with a force in the direction of the axial bearing are arranged between the shank and the inner shank. The further object, in particular, is achieved by an instrument in which a fiber-optics guide is provided at least in the region of the handle part and seals the space in which the fiber-optics are led through the handle part in a diffusion-tight manner with respect to the inside of the handle part. Advantageous embodiments of the invention may be deduced from the dependent claims, the following description and the drawings.

The optical instrument according to the invention, typically an endoscope or a technoscope, comprises an outer shank on or near whose free shank end a viewing window is provided, wherein this shank with its other end is fastened in a handle part. An opto-electric transducer, for example a CCD-element, is arranged within the shank. This transducer is rotatably arranged within the outer shank, and is incorporated with an inner shank rotatably mounted in the outer shank. Actuation means are provided for rotating the transducer in the outer shank, typically on the handle part. According to the invention, an axial bearing is provided between the outer shank and the inner shank, which carries the transducer, and furthermore at least one spring element is provided impinging the inner shank in the direction of the axial bearing with force. This solution according to the invention ensures that the transducer together with the inner shank in which it is fastened, although being able to be guided in a movable manner with a comparatively large play in the axial direction of the shank, is however always impinged by force in the direction of the axial bearing on account of the spring element, and is thus always located in a defined position. Since the transducer element is arranged as far as possible in the distal direction, thus directly in front of the optics located in the outer shank, this distance, which is important with regard to the imaging definition, in practice does not change, even with changes in length within the instrument which are induced thermally. On the other hand, the inner shank and the outer shank may rotate and move freely with respect to one another without changing this defined distance, which is constantly given due to the abutment of the axial bearing.

An axial bearing in the context of the present invention is a bearing which accommodates forces which occur in the direction of the longitudinal axis of the shank. This, however, does not rule out the bearing also being effective in a radial manner. A shank, inner shank and outer shank, in the context of the present invention, are to be understood as tubular bodies as are typically applied in endoscopic instruments, and are arranged lying in one another or next to one another.

The present invention is advantageously applicable to instruments with lateral viewing optics, but does not exclude the application for other optics.

In order to mount the inner shank over its length in a precise manner, according to a further embodiment of the invention, it is envisaged apart from the axial bearing, to provide a further bearing, preferably a radial bearing, wherein the axial bearing is arranged close to the transducer, and the further bearing, thus the radial bearing, is arranged close to the handle part, preferably within the handle part. A precise guiding within the shank results for the inner shank in this manner, even with a large expansion in length. Here, the radial bearing may be designed in a simple form as a ball bearing, and may be arranged such that an axial length compensation between the inner shank and the outer shank may be effected in this region.

The spring element may advantageously be formed by a helical spring which is preferably arranged in the region of the handle part, surrounds the inner shank at a small distance, and which on the one hand is supported on the further bearing connected to the inner shank, and on the other hand within the handle part. The spring force thus acts on the bearing which is firmly connected to the inner shank, and is displaceably guided within the handle part in the longitudinal direction of the shank. Here, the helical spring is arranged on that side of the further bearing which is distant to the axial bearing, so that the force effect is always directed in the direction of the axial bearing.

According to a further advantageous embodiment of the invention, the outer shank of the instrument is fixed in the handle part, wherein the inner shank projects beyond the outer shank on the proximal side in this region, i.e., projects into the handle part significantly further than the outer shank. This is particularly favorable since then, on the one hand, sufficient space remains for the arrangement of the further bearing and the spring, and on the other hand further space remains for the design formation of the actuation means for rotating the inner shank with respect to the instrument.

The axial direction itself is advantageously formed by two bearing rings of which one is fixed on the outer shank side, and the other on the inner shank side. The bearing rings are preferably manufactured of ceramic material, so that the bearing on the one hand is temperature resistant, and on the other hand operates without lubricants, and in a manner which is low in friction and wear.

The inner shank is advantageously formed by a cylindrical tube, which extends from the handle part far into the outer shank, and which at its end close to the transducer, is connected in a longitudinally adjustable manner in the shank direction, to a hollow body accommodating the transducer. Any manufacturing tolerances may be compensated by this arrangement, and in particular, the transducer may be aligned and fixed to the optics in the axial direction on assembly.

According to a further embodiment of the invention, the stationary bearing ring of the axial direction is not fixed directly on the outer shank, but on that end of a sleeve which faces the handle part, the sleeve for its part being firmly connected to the outer shank, preferably by welding.

The rotatable bearing ring of the axial bearing is advantageously also not connected to the inner shank in a direct manner, but is fixed on that end of a bushing which faces away from the handle part, the bushing being firmly connected to the inner shank. This bushing projects beyond that end of the inner shank which is close to the transducer, and is advantageously welded to this. Here, this bushing advantageously not only engages over the transducer-side end of the inner shank, but also the oppositely lying end of the hollow body accommodating the transducer, and furthermore comprises means for the preferably detachable fastening of the hollow body. Typically, a grub screw is admitted in a transverse bore of the bushing, which is screwed in after the axial alignment of the components to one another, and thus fixes the hollow body which carries the transducer, with respect to the inner shank.

In order to be able to seal the instrument in a hermetically tight manner, thus to be able to make do without seals prone to wear, in a further embodiment of the invention, it is intended to provide the coupling between the inner shank on the one hand and an adjustment ring rotatably arranged on the handle part on the other hand, in a magnetic manner. Such an arrangement is described in detail in German Patent DE 195 21 654 C2, and this is hereby incorporated expressly by reference.

The instrument according to the invention with a suitable design may be completely hermetically sealed, and specifically basically without seals. Thus, for example, the distal viewing window, in a manner known per se, may be connected to the shank with a material fit by soldering, just as the handle part by the use of a magnetic coupling may comprise a closed metallic sleeve. However, the leading-through of the fiber-optics often presents a problem, since the fiber-optics bundle which is guided through the instrument from the fiber-optics connection on the handle part up to the distal end of the shank part, although being embedded at the ends in a plastic/adhesive filling the space between the fiber-optics, this material however, as with almost all plastics, is not completely impermeable to vapor. Thus, vapor may diffuse into this region in the course of time, which is undesirable.

According to a further embodiment of the present invention, it is therefore intended to arrange the fiber-optics within the handle part within a fiber-optics guide, wherein this fiber-optics guide is sealed with respect to the inside of the handle in a pressure-tight manner. In a further embodiment of the invention, this is effected in the outer shank region in an analogous manner in that the light guides, in the region of the outer shank, are guided between the shank and a further outer shank surrounding this. Since the outer shank itself typically consists of metal, in particular stainless steel, this is diffusion-tight, and an entry of vapor by this path also is ruled out.

By the diffusion-tight leading of the fiber-optics in the handle part and in the shank part, it is then also ensured that the handle part as well as the shank are designed in a completely diffusion-tight manner with respect to the space which leads the fiber-optics bundle.

In order to achieve a complete sealing with regard to diffusion, it is necessary to design the fiber-optics guide in a metallic manner, typically of stainless steel. In order to permit any occurring length expansions, and also to have a certain amount of play in the case of repair, it is useful to interrupt the fiber-optics guide between the actual handle part and the shank, and to provide a free space here, in which the fiber-optics bundle runs in a sickle-like manner, and thus certain length extensions—be they caused by temperature or repair—may be accommodated.

It is further useful to provide a bellows in the fiber-optics guide in the region of the handle part, which is provided particularly for compensating length changes caused by repair, if for example the handle part is cut open for repair purposes and welded again after the repair has been effected, since then the length of the handle part may change and thus an adaptation in the region of the fiber-optics guide is necessary. The remaining fiber-optics guide is advantageously tubular and is formed of metal, is welded at the connection ends to the bellows likewise consisting of metal, as well as connected at the end to the handle part by welding.

BRIEF DESCRIPTION OF THE SEVERAL VIEWS OF THE DRAWINGS

The foregoing summary, as well as the following detailed description of the invention, will be better understood when read in conjunction with the appended drawings. For the purpose of illustrating the invention, there are shown in the drawings embodiments which are presently preferred. It should be understood, however, that the invention is not limited to the precise arrangements and instrumentalities shown. In the drawings:

FIG. 3 is an enlarged sectional representation of the inner distal end of the handle part according to the embodiment of FIG. 1; and FIG. 4 is an enlarged representation of a shank section in longitudinal section.

DETAILED DESCRIPTION OF THE INVENTION

Figure 1:
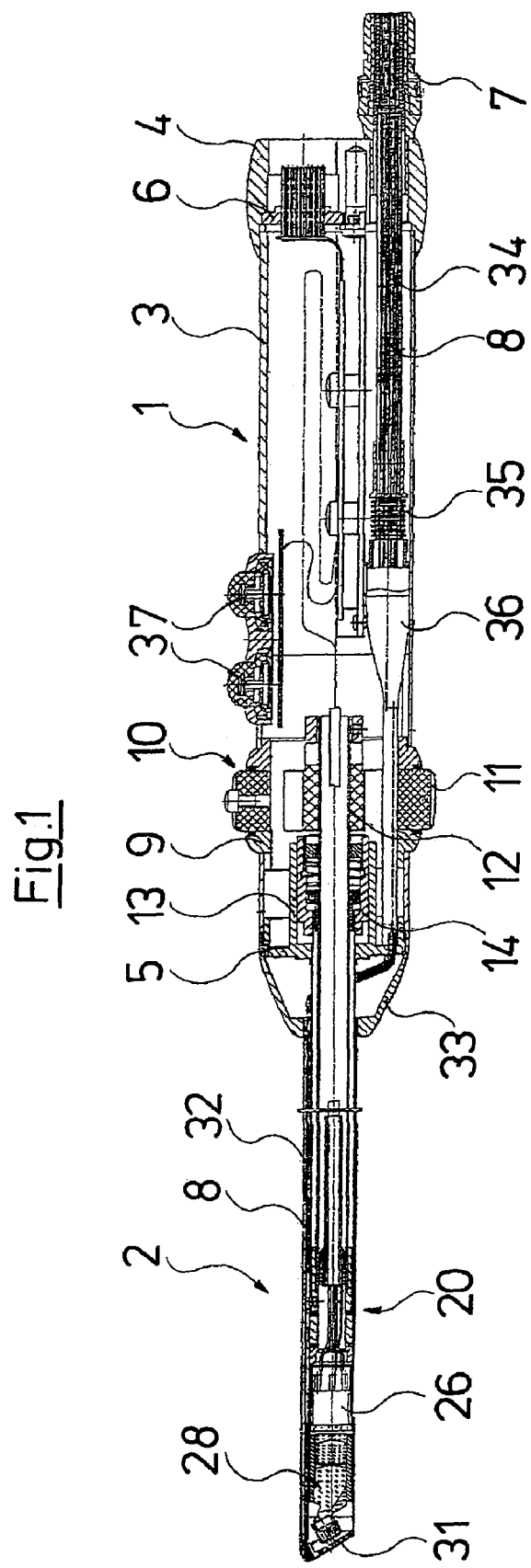
FIG. 1 is a longitudinal section through an endoscopic instrument according to one embodiment of the invention.
Figure 2:
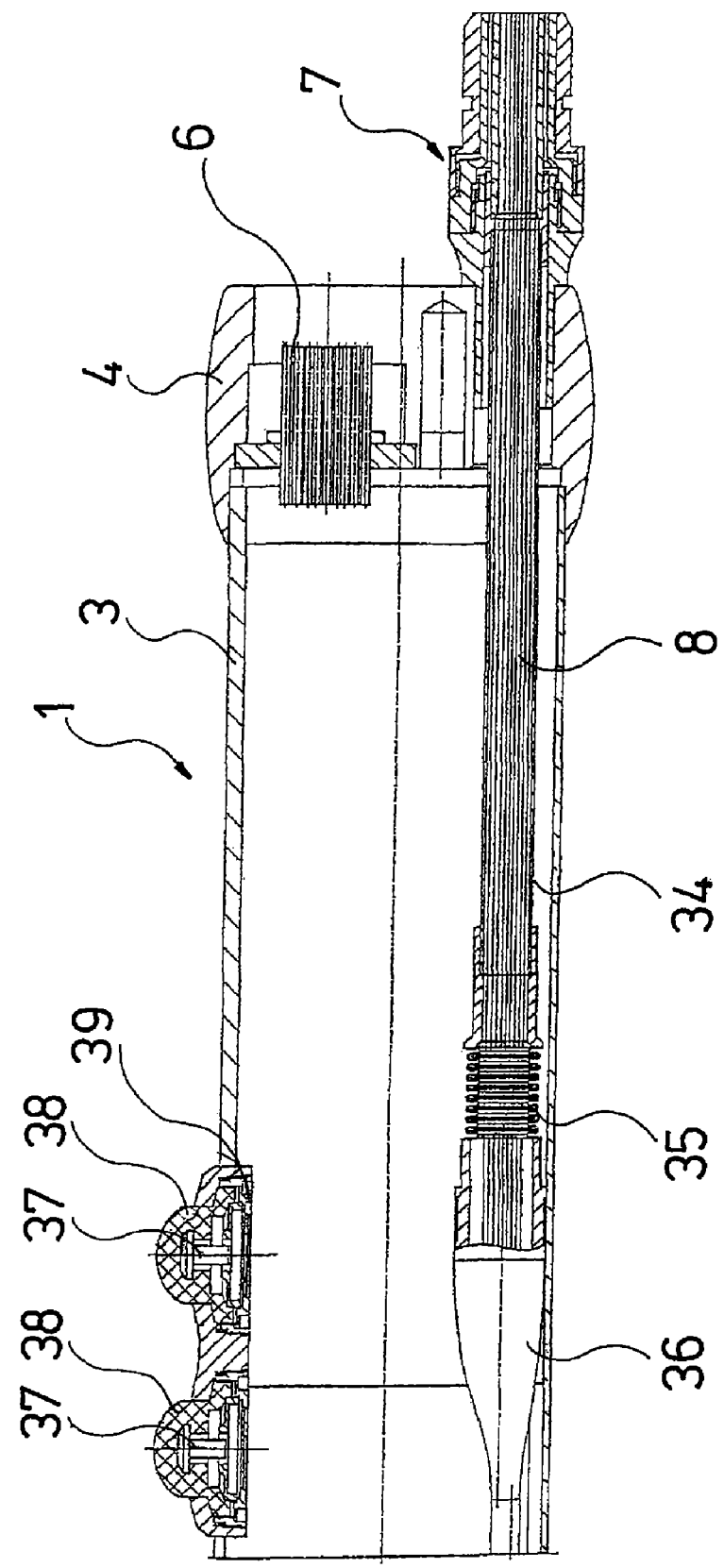
FIG. 2 is an enlarged, simplified, sectional representation of the proximal end of the handle part according to the embodiment of FIG.

With the instrument represented by the drawings, there is shown an endoscope having a handle part 1 and a shank part 2. The shank part 2 is shown in a shortened manner in FIG. 1 and serves for introduction into a natural body cavity or a cavity created artificially. The handle part 1 consists essentially of a cylindrical tube section 3, which on the proximal end is sealingly closed by a closure part 4, which engages over the proximal end and is welded on the tube section 3. On the distal end, the tube section 3 is closed off by a distal closure part 5, which is likewise connected thereto in a diffusion-tight manner by welding.

A ceramic connection lead-through 6 for leading out all electrical leads, and which is soldered into the metallic closure part 4, is provided in the proximal closure part. Furthermore, a fiber-optics cable connection piece 7, which is designed in a manner known per se and in the inside carries a bundle of fiber-optics fibers 8, whose intermediate spaces are filled in a flush manner with plastic, is welded in the proximal closure part 4.

The cylindrical tube section 3 is interrupted in the distal-end part by the stationary part 9 of a magnetic coupling 10. The design and the operation of this magnetic coupling are described in German Patent DE 195 21 654 C2, and this document is referred to with regard to the magnetic coupling. An adjustment ring 11 is rotatably mounted on the stationary part 9, and is sealed with respect to the stationary part 9 by seals. The seals do not seal with respect to the inside of the handle part 1, but merely with respect to the space formed between the adjustment ring 11 and the stationary part 9. The handle part in this region is sealed in a diffusion-tight manner by the stationary part 9 and by the tube section 3 connecting thereto on opposite sides. The adjustment ring 11 carries on its inner side a magnet (not represented in detail) which cooperates with another magnet (likewise not shown in detail) arranged on an inner shank 12 in this region.

This inner shank 12 is rotatably mounted within the instrument. For this purpose, the distal closure part 5 comprises a hollow-cylindrical section 13, which extends proximally into the handle part 1 and which is firmly connected to a sleeve 14. The sleeve 14, on the distal end, carries a shank 15 surrounding the inner shank 12 in the whole shank part 2 and being stationary.

Furthermore, a ball bearing 16 is displaceably guided within the sleeve, and its inner ring on the distal end bears on the end of an inner sleeve 17, which is firmly connected to the inner shank 12. A helical spring 18 is arranged within the sleeve 14, and on the one hand is supported on the ball bearing 16 and on the other hand on a screw 19 whose outer thread is fixed in the inner thread of the sleeve 14. The screw 19 has a central through-bore through which the inner shank 12 is movably guided with play.

The inner shank 12, which is radially guided in the handle part 1 by the ball bearing 16, extends far into the shank part 2, and there is guided in an axial bearing 20 in the axial direction of the shank part 2. The axial bearing 20 also accommodates the forces of the helical spring 8 which constantly act on this and which are transmitted by the inner shank 12. The axial bearing 20 is formed by two ceramic bearing rings 21 and 22. The bearing ring 21, co-rotating with the inner shank 12, is fastened on the distal end of a bushing 23, which projects beyond the distal end of the inner shank 12 and is firmly connected to this. The stationary bearing ring 22 is fastened on the proximal end of a sleeve 24, which is firmly connected to the shank 15.

A tubular, distally shouldered hollow body 25, which carries a CCD-element 26, is incorporated within the bushing 23 as well as the distal end of the inner shank 12. This hollow body 25 is mounted within the sleeve 24 with play. Within the bushing 23, the hollow body 25 is fixed with respect to the inner shank 12 by a grub screw 27 arranged there in a transverse bore. This grub screw 27 is only rotated in when the longitudinal alignment of the CCD-element 26 with respect to the distal-end optics 28 has been effected, so that it is ensured that the CCD-element 26 is always arranged at the envisaged location for producing a sharp image. The hollow body 25 is fixed with respect to the bushing 23 and the inner shank 12 which is firmly connected thereto, after rotating in the grub screw 27. A recess 29 is provided in the shank 15 in order to reach the grub screw 27. In order to close the recess 29, a further shank 30 is stuck over the shank 15 and is welded to this on the distal end of the recess 29, as well as on the proximal end. The distal end of the shank 15 is closed off by a window 31, which is arranged obliquely to the longitudinal axis and which is soldered into the shank 15 in a diffusion-tight manner. The associated lateral viewing optics 28 lying behind this are known per se and therefore not described in detail here.

With the previously described design, the inner shank 12 may be rotated with respect to the instrument by rotating the adjustment ring 11 via the magnetic coupling 12, in order to effect a tracking of the CCD-element 26 when the instrument has been rotated about its longitudinal axis. The axial forces are thereby always accommodated by the axial bearing 20, wherein the helical spring 18 ensures that the inner shank 12 is always impinged by force in the direction of the distal instrument end. Thus even with heating, it is ensured that the inner shank 12 may expand in the longitudinal direction, but on the other hand that the distance between the CCD-element 26 and the optics 28 remains practically unchanged.

The fiber-optics fibers in the region of the shank part 2 are led between the shank 15 or the shank 30 covering these, and an outer shank 32, wherein the outer shank 32 is arranged eccentrically to the shank 15, so that in the representations according to FIGS. 1 and 4, a free space for the fiber-optics fibers 8 results in the shank part 2 at the top. The fiber-optics fibers 8 end at the end next to the window 31 on the other side of the shank 15, so that the shank 15 is sealed in a diffusion-tight manner with respect to the fiber-optics fiber channel formed there.

The handle part 1 is closed off on the distal end by a cap 33, which on the one hand is welded to the distal closure part 5, and on the other hand is connected by welding to the proximal end of the outer shank 32. A space, which is sealingly closed off with regard to the shaft part 2, on the one hand, and with respect to the handle part 1, on the other hand, thereby results within the space surrounded by the cap 33. This space merely serves for leading through the fiber-optics fibers 8, and the fiber-optics fibers 8 are led around the shank 15 in a sickle-like manner, A recess is provided within the distal closure part 5. The fiber-optics fiber bundle 8 in FIG. 1 on the lower side of the handle part 1 comes into the inside of this recess and here is guided roughly parallel to the tube section 3 on the lower side, up to the fiber-optics cable connection piece 7. Within the region from the distal closure part 5 to the proximal closure part 4, the fiber-optics fibers 8 are led within a fiber-optics fiber guide of metal, so that this space is formed diffusion-tight with respect to the inside of the handle part 1. The guiding is thereby effected from the proximal closure part 4, first through a cylindrical guide tube 34, then through a metallic bellows 35 and finally through an enveloping piece 36. The piece 36 leads the fiber strand, which is round in cross section, into a flattened channel extending over a part circle along the tube section 3, and is adapted to the curvature of the tube section 3. This partly flattened enveloping piece 36, adapted to the rounding of the tube section 3, serves for leading the fiber-optics fibers 8 through the region of the magnetic coupling 10, without having to increase the distances between the magnets which are provided there. A lead-through, which is as flat as possible, is thus formed there. The fiber-optics guide at the ends is welded to the closure parts 4, 5, which are connected in each case.

Two press buttons 37 are arranged on the upper side of the handle part 1. The buttons carry on their lower side carry a magnet, and on their upper side are covered by an elastic plastic 38. The switch housing is closed off below the magnets by a thin sheet plate 39, which is connected to the tube section 3 in a pressure-tight manner by welding. A circuit board with hall elements is arranged below this sheet plate 39, so that a switching procedure may be activated through the sheet plate 39 by one of the buttons 37. The further electronics are arranged within handle part 1. The switch function of the press buttons 37 is freely programmable, for example for activating a white matching of the video camera or other functions.

For repair purposes, the handle part 1 may be opened by breaking open the tube section 3 in the region between the switch 37 and the stationary part 9. In order then to be able to pull apart the separated housing halves to such an extent that the components located therein, be they the electronics or the shaft-side components, are able to be reached, it is necessary to pull the shank halves apart. The bellows 35 is necessary for this and permits the components to be pulled part without breaking open the fiber-optics guide. Furthermore, with a later welding of the handle part 1 by peripheral welding, the bellows 35 also serves for the compensation of any occurring length changes of the handle part 1.

The fiber-optics bundle 8 is therefore sealed within the handle part 1 in a diffusion-tight manner with respect to the remaining inside of the handle part 1. Only in the region of the cap 33 do the fiber-optics 8 lie freely in the space. However, this space is sealed in a diffusion-tight manner with respect to the handle part as well as the shanks 15 and 30. The fiber-optics bundle 8 is guided in an eccentric manner between the shanks 15 or 30 and the outer shank 32 within the shank part, so that the actual endoscopic instrument is sealed with respect to the fiber-optics fiber bundle 8 as well as with respect to the outer atmosphere, in a hermetic and diffusion-tight manner. All connections are formed with a material fit by soldering or welding.

It will be appreciated by those skilled in the art that changes could be made to the embodiments described above without departing from the broad inventive concept thereof. It is understood, therefore, that this invention is not limited to the particular embodiments disclosed, but it is intended to cover modifications within the spirit and scope of the present invention as defined by the appended claims.

We claim:

1. An optical instrument comprising: an outer shank (15) having a viewing window (31) arranged close to a free end of the outer shank and a handle part (1) on an opposite end of the outer shank; a longitudinal axis of the outer shank extending from the free end of the outer shank to the opposite end of the outer shank; an opto-electrical transducer (26) rotatably arranged within the outer shank (15) and attached on an inner shank (12), the inner shank being rotatably mounted within the outer shank; the outer shank being fixed in the handle part and the inner shank projecting proximally beyond the outer shank in a region of the handle part; actuation means (10) for rotating the transducer (26) in the outer shank (15); and an axial bearing (20) and at least one spring element (18); a longitudinal axis of the at least one spring element (18) extending parallel to the longitudinal axis of the outer shank, the at least one spring element (18) impinging the inner shank (12) with force in a direction of the axial bearing (20) and the longitudinal axis of the outer shank; the axial bearing and the at least one spring element being arranged between the outer shank (15) and the inner shank (12).

2. The optical instrument according to claim 1, wherein the inner shank (12) is mounted in a rotatable manner within the instrument by a radial ball bearing (16), and wherein the axial bearing (20) is arranged close to the transducer and the radial ball bearing (16) is arranged within the handle part (1).

3. The optical instrument according to claim 2, wherein the at least one spring element (18) comprises a helical spring (18) which surrounds an entire periphery of at least a portion of the inner shank (12) and which is supported on an inner shank side of the radial ball bearing (16) and within the handle part (1).

4. The optical instrument according to claim 1, wherein the axial bearing (20) comprises two bearing rings (21, 22).

5. The optical instrument according to claim 4, wherein the two bearing rings (21, 22) comprise ceramic.

6. The optical instrument according to claim 5, wherein one of the bearing rings is a stationary bearing ring (22) fixed on an end of a sleeve (24) facing the handle part (1), the sleeve being firmly connected to the outer shank (15).

7. The optical instrument according to claim 5, wherein one of the bearing rings is a rotatable bearing ring (21) fastened on an end of a bushing (23) which facing away from the handle part (1), the bushing being firmly connected to the inner shank (12).

8. The optical instrument according to claim 7, wherein the bushing (23) engages over a distal end of the inner shank (12) and an opposite end of a hollow body (25) accommodating the transducer (26), and wherein means (27) are provided in the bushing (23) for detachable fastening of the hollow body (25) on the bushing (23).

9. The optical instrument according to claim 1, wherein the inner shank (12) comprises a cylindrical tube extending from the shank (15) up to the handle part (1), and wherein the cylindrical tube is connected at its end close to the transducer, in a manner which is longitudinally adjustable in a shank direction relative to a hollow body (25) accommodating the transducer.

10. The optical instrument according to claim 1, wherein the inner shank (12) is magnetically coupled to an adjustment ring (11) rotatably arranged on the handle part (1).

11. The optical instrument according to claim 1, wherein fiber-optics (8) are led through the instrument, and wherein a fiber-optics guide (34, 35, 36) is provided at least in a region of the handle part (1) to seal a space in which the fiber-optics (8) are led through the handle part (1) in a diffusion-tight manner with respect to an inside of the handle part (1).

12. The optical instrument according to claim 11, wherein a portion of the fiber-optics guide (34, 35, 36) located within the handle part (1) comprises a bellows (35) for compensation of changes in length caused by repair.

13. The optical instrument according to claim 11, wherein the fiber-optics guide (34, 35, 36) comprises a metal tube, and wherein both ends of the fiber-optics guide are connected to the handle part (1) by welding.

14. The optical instrument according to claim 1, wherein the fiber-optics (8) in a region of the outer shank are guided between the outer shank (15), which is diffusion-tight and a further outer shank (32) surrounding the outer shank (15).

15. The optical instrument according to claim 1, wherein the instrument is an endoscope.

16. The optical instrument according to claim 1, wherein the instrument is a technoscope.

17. An optical instrument comprising: an outer shank (15) having a viewing window (31) arranged close to a free end of the outer shank and a handle part (1) on an opposite end of the outer shank; an opto-electrical transducer (26) rotatably arranged within the outer shank (15) and attached on an inner shank (12), the inner shank being rotatably mounted within the outer shank; actuation means (10) for rotating the transducer (26) in the outer shank (15); and an axial bearing (20) and at least one spring element (18) impinging the inner shank (12) with force in a direction of the axial bearing (20); the axial bearing comprising two ceramic bearing rings (21, 22); the axial bearing and the at least one spring element being arranged between the outer shank (15) and the inner shank (12).

18. The optical instrument according to claim 17, wherein one of the bearing rings is a stationary bearing ring (22) fixed on an end of a sleeve (24) facing the handle part (1), the sleeve being firmly connected to the outer shank (15).

19. The optical instrument according to claim 17, wherein one of the bearing rings is a rotatable bearing ring (21) fastened on an end of a bushing (23) which facing away from the handle part (1), the bushing being firmly connected to the inner shank (12).

20. The optical instrument according to claim 19, wherein the bushing (23) engages over a distal end of the inner shank (12) and an opposite end of a hollow body (25) accommodating the transducer (26), and wherein means (27) are provided in the bushing (23) for detachable fastening of the hollow body (25) on the bushing (23).

* * * * *